United States Patent [19]

Summer

[11] Patent Number: 5,505,618
[45] Date of Patent: Apr. 9, 1996

[54] TOOTH SPACER

[76] Inventor: John D. Summer, 14982 NW. Mill Rd., Portland, Oreg. 97231

[21] Appl. No.: 253,113

[22] Filed: Jun. 2, 1994

[51] Int. Cl.⁶ .................................................. A61C 7/00
[52] U.S. Cl. .................................................. 433/148
[58] Field of Search .................... 433/39, 40, 155, 433/226, 148, 149, 140, 142

[56] References Cited

U.S. PATENT DOCUMENTS

| | | | |
|---|---|---|---|
| 638,973 | 12/1899 | Mehlig | 433/40 |
| 804,099 | 11/1905 | Chase | 433/39 |
| 3,305,928 | 2/1967 | Tofflemire | 433/39 |
| 4,373,915 | 2/1983 | Comstock | 433/136 |
| 5,330,353 | 6/1994 | Wavrin | 433/39 |
| 5,342,194 | 8/1994 | Feldman | 433/39 |

*Primary Examiner*—Cary E. O'Connor
*Attorney, Agent, or Firm*—Klarquist Sparkman Campbell, Leigh & Whinston

[57] ABSTRACT

The tooth spacer comprises an elongated body having two opposite side edges extending between gingival and occlusal edges. A recessed or thin central portion of the body extends from the gingival edge toward the occlusal edge. The recessed central portion is sufficiently thin so that it may be inserted between the interproximal surfaces of two adjacent teeth while minimizing any wedging of the teeth apart.

22 Claims, 1 Drawing Sheet

5,505,618

TOOTH SPACER

FIELD OF THE INVENTION

The present invention relates to the field of dental devices and particularly to tooth spacers placed between teeth.

BACKGROUND OF THE INVENTION

In the field of dentistry, stainless steel and plastic strips of various kinds have been used for many years for separating adjacent teeth during restorative dental procedures such as when filling a cavity. The strips are placed between the interproximal surfaces of a pair of adjacent teeth to provide protection from injury to an adjacent tooth while one tooth is treated. For example, U.S. Pat. No. 4,373,915 to Comstock discloses a resilient stainless steel band having a uniform thickness. The band is bendable into a U-shape to contact the buccal and lingual surfaces of a tooth while the adjacent tooth is treated.

Conventional strips known to the inventor have been at least ten microns in thickness and wedge the teeth apart slightly. This wedging has not been a problem when used with amalgam filling material packed between two adjacent teeth.

However, new aesthetically pleasing and structurally strong materials have been developed such as composite resin materials. One drawback of the new composite resin materials is that they cannot be packed as easily into a tooth cavity as amalgam. Therefore, the teeth are typically wedged further apart to permit packing of this material. Consequently, relatively thick tooth spacers have been used to accomplish this desired wedging. As a result, following filling and when the strips are removed, a small space or gap is left between the teeth. Any such gap or interproximal space, even when very small, is a trap for food to lodge between the teeth during chewing. This contributes to tooth cavities and gum diseases, such as periodontal disease.

Recently, composite resins have been bonded to the teeth for the purpose of correcting the bite of a patient. The composite resin may be applied to the upper surface of several teeth simultaneously and the mouth then closed in the desired therapeutic jaw position to establish the proper bite. With this approach, it is difficult to prevent the composite resin from ending up in the interproximal space between the teeth and it is also difficult to remove this resin from this space once it is there. Yet, if conventional interproximal strips are used between the teeth, they wedge adjacent teeth apart and thereby slightly change the positions of the teeth. When these strips are removed following the resin bonding treatment, the teeth return to their unwedged positions, which makes the bite no longer as accurate as desired.

A need remains for a tooth spacer which, contrary to the approach of the prior art, virtually eliminates wedging of teeth apart during use.

SUMMARY OF THE INVENTION

The invention comprises a tooth spacer including an elongated body. The body has opposite side edges extending between an occlusal edge and an gingival edge. A central portion of the body is of a reduced thickness and preferably extends from the gingival edge toward the occlusal edge. The area of the body bounding the central portion is thicker than the central portion for reinforcing purposes. The central portion may be placed between the contact areas of adjacent teeth virtually without wedging the teeth apart.

DETAILED DESCRIPTION OF THE INVENTION

Figure 1:
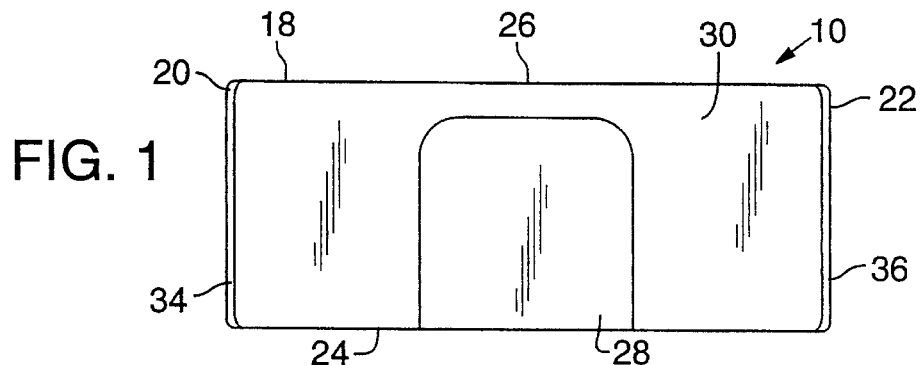
FIG. 1 shows a side view of an illustrated embodiment of the tooth spacer of the present invention.
Figure 2:
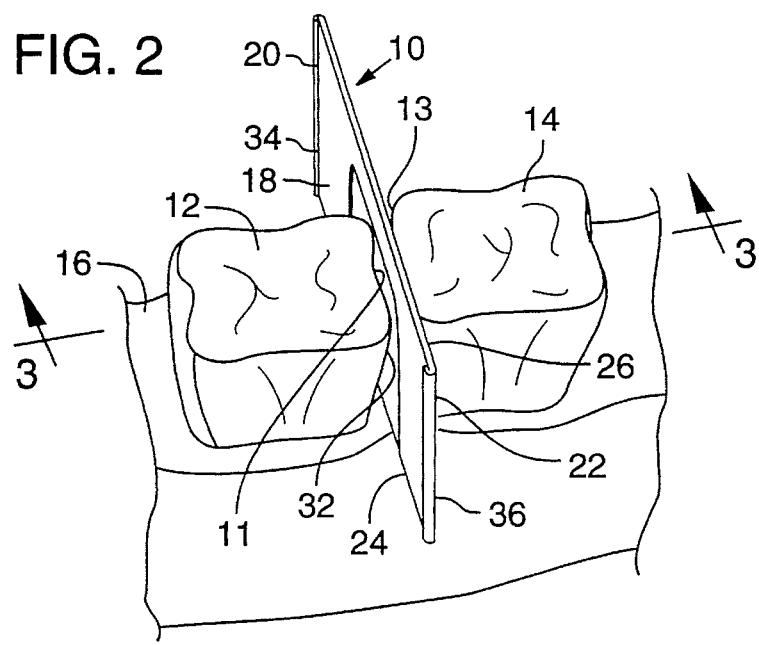
FIG. 2 shows a perspective of the illustrated embodiment of the tooth spacer positioned between a pair of teeth.
Figure 3:
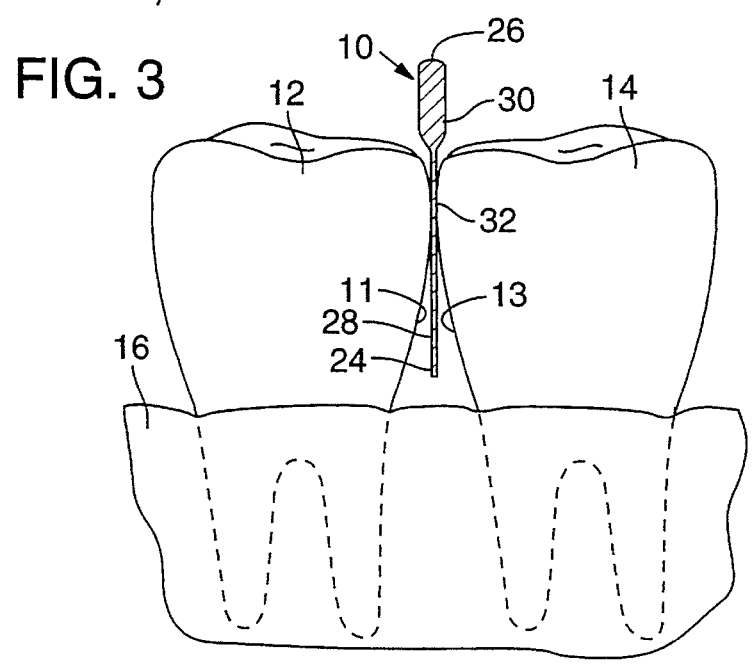
FIG. 3 shows a side view of a pair of teeth with the spacer of FIG. 1.

FIGS. 1–3 illustrate one embodiment of a tooth spacer 10 of the present invention. The tooth spacer 10 may be inserted between interproximal surfaces 11, 13 (best seen in FIG. 3), respectively, of a tooth 12 to be treated, and an adjacent tooth 14. The illustrated teeth 12, 14 each have a root extending into the gum 16 of a patient's jaw. The tooth spacer 10 may be of any shape, but typically comprises an elongated body 18 having a pair of opposite transversely spaced sidewalls or edges 20, 22 and a gingival edge 24 and an occlusal edge 26. The term "gingival edge" refers to the edge of the body positioned closest to the patient's gum when the spacer is inserted in place. The elongated body 18 has a recessed or thin central portion 28 at least partially surrounded or enclosed by a peripheral portion 30. The body 18 is preferably of a monolithic or unitary construction and is most preferably, but not necessarily, made of a durable material such as stainless steel. Of course, the body may be of a multiple piece construction and may also be made of other materials such as wood, ceramics and polymeric materials.

In the illustrated preferred embodiment, the tooth spacer is generally rectangular with side walls or edges 20, 22 being from about ¼ to ⅜ inch long and the edges 24, 26 about ½ to ¾ inch long. The thickness of the peripheral or reinforcing portion 30 of the body 18 may range from about 0.0015 to 0,003 inch, although it may be thicker. As a result, the tooth spacer is sufficiently resilient or elastic to leave some memory when bent during insertion. Also, the spacer is flexible so that it may be bent to conform to the tooth shape during insertion. For a stainless steel tooth spacer with a reinforcing portion of this thickness, typically the reinforcing portion must be at least about 3/32 inch wide between the top of the recessed central portion and the adjacent occlusal edge 26 to strengthen the space 10 in this region. With other materials or thicker reinforcing materials, the width of the reinforcing portion may be varied. Functionally, the reinforcing portion needs to be strong enough to prevent the recessed or thin portion of the tooth spacer from tearing during insertion between teeth and to provide sufficient rigidity to facilitate insertion of the tooth spacer, e.g. by pushing down on the occlusal edge of the spacer as it is inserted. Other dimensions may be used.

The side walls or edges 20, 24 may optionally be rolled to form respective rounded lips 34, 36 to eliminate sharp edges that could injure a patient's tongue, cheek, or other parts of the mouth when the tooth spacer 10 is placed between adjacent teeth. These enlarged side edges or lips may alternatively be formed in any suitable manner, such as by securing an elongated polymer or rubber bead or other material to the side edges of the tooth spacer. One approach is simply to dip each of the side edges in polymer and allow the polymer to solidify to form the rounded lips.

The thin central portion 28 preferably has a thickness ranging from 0.0001 to 0,001 inch. As a result, the tooth spacer may be positioned between the interproximal surfaces 11, 13 of the two adjacent teeth 12, 14 while virtually eliminating any wedging of the teeth apart. The central portion 28 is of a material that is sufficiently rigid to withstand being forced down between the adjacent teeth 12, 14 at a contact area 32. The central portion 28 of the preferred embodiment extends from the gingival edge 24 to a location adjacent the occlusal edge 26 such as between 1/32 and 1/8 inch from the edge 26. The thinned central portion is preferably dimensioned to be larger than the contact area 32. As is apparent, the central portion 28 may extend all the way to the occlusal edge 26. However, it is preferred to have a thicker reinforcing portion of the tooth spacer bounding the central portion. The thin central portion 28 may be made by either a grinding, molding, casting, chemical etching, stamping or any other process suitable for achieving a recessed or thinned area. A grinding process is presently preferred.

The central portion in the illustrated embodiment is preferably from about one-eighth inch to about three-eighths inch wide, as this is wider than the width of the contacting interproximal surfaces of most pairs of teeth. Also, the height or distance the central portion extends from the gingival edge is typically from seventy-five to ninety-five percent of the overall height of the tooth spacer. In most cases, the central portion is from about one-eighth to about three-sixteenths of an inch high.

Again, the peripheral portion 30 has a thickness greater than the thickness of the central portion 28 to provide reinforcement and rigidity to the tooth spacer 10. The illustrated peripheral portion 30 extends between the central portion 28 and the respective side walls or edges 20, 22 and between the central portion 28 and the occlusal edge 26. A reinforcing portion 30 may also be positioned along the gingival edge of the tooth spacer as this edge ends up in the gap below the contacting areas of the teeth after the tooth spacer has been inserted. However, this is less preferred because it would make the tooth spacer more difficult to insert.

While the present invention has been described in accordance with a preferred embodiment, it is to be understood that substitutions and alterations may be made thereto without departing from the spirit and scope of the claims. I claim all such modifications which fall within the following claims.

I claim:

1. A tooth spacer for insertion between the interproximal surface of a pair of adjacent teeth during a dental procedure, the teeth having a proximate area where the teeth are closest to or in contact with one another, the tooth spacer comprising:

a monolithic body having a first thickness, the body having respective opposite gingival and occlusal edges and opposite side edges extending between the gingival and occlusal edges; and the body including a central portion extending from the gingival edge toward the occlusal edge and the central portion being spaced from the occlusal edge, the central portion having a second thickness which is less than the first thickness, the central portion being positioned between the interproximal surfaces of adjacent teeth when the tooth spacer is between the teeth.

2. A tooth spacer according to claim 1 wherein the body is made of a resilient material.

3. A tooth spacer according to claim 2 wherein the resilient material is stainless steel.

4. A tooth spacer according to claim 1 wherein the body is rectangular.

5. A tooth spacer according to claim 1 wherein the central portion is rectangular.

6. A tooth spacer for insertion between the interproximal surface of a pair of adjacent teeth during a dental procedure, the teeth having a proximate area where the teeth are closest to or in contact with one another, the tooth spacer comprising:

a body having a first thickness, the body having respective opposite gingival and occlusal edges and opposite side edges extending between the gingival and occlusal edges;

the body including a central portion extending from the gingival edge toward the occlusal edge and the central portion being spaced from the occlusal edge, the central portion having a second thickness which is less than the first thickness, the central portion being positioned between the interproximal surfaces of adjacent teeth when the tooth spacer is between the teeth, and wherein the side edges are provided with rounded lips.

7. A tooth spacer for insertion between the interproximal surface of a pair of adjacent teeth during a dental procedure, the teeth having a proximate area where the teeth are closest to or in contact with one another, the tooth spacer comprising:

a body having a first thickness, the body having respective opposite gingival and occlusal edges and opposite side edges extending between the gingival and occlusal edges;

the body including a central portion extending from the gingival edge toward the occlusal edge and the central portion being spaced from the occlusal edge, the central portion having a second thickness which is less than the first thickness, the central portion being positioned between the interproximal surfaces of adjacent teeth when the tooth spacer is between the teeth; and wherein the second thickness is from 0.0001 to 0.001 inch.

8. A tooth spacer according to claim 7 wherein the central portion is from one-eighth to three-eighths inch wide.

9. A tooth spacer according to claim 8 wherein the central portion extends to a height which is seventy-five percent to ninety-five percent of the height of the tooth spacer.

10. A tooth spacer according to claim 8 in which the central portion is from one-eighth to three-sixteenth inch high.

11. A tooth spacer for insertion between the interproximal surface of air of adjacent teeth during a dental procedure, the teeth having proximate area where the teeth are closest to or in contacting one another, the tooth spacer comprising:

a body having a first thickness, the body having respective opposite gingival and occlusal edges and opposite side edges extending between the gingival and occlusal edges;

the body including a central portion extending from the gingival edge toward the occlusal edge, the central portion having a second thickness which is less than the first thickness, the central portion being positioned between the interproximal surfaces of adjacent teeth when the tooth spacer is between the teeth, wherein the second thickness is from 0.0001 to 0.001 inch, the central portion is from one-eighth to three-eighths inch wide, the central portion is from one-eighth to three-sixteenth inch high, and wherein the central portion is bounded along the side edges and occlusal edge of the body by a reinforcing portion of the first thickness, the body reinforcing portion being at least one-thirty-second inch wide.

12. A tooth spacer for insertion between the interproximal surface of a pair of adjacent teeth during dental procedure, the teeth having a proximate area where the teeth are closest to or in contact with one another, the tooth spacer comprising:

a body having first thickness from 0.0015 to 0.003 inch thick, the body having respective opposite gingival and occlusal edges and opposite side edges extending between the gingival and occlusal edges; and the body including a central portion from one-eighth to three-eighths inch wide and extending form the gingival edge toward the occlusal edge, the central portion being one-eighth to three-sixteenth inch high and being spaced from the occlusal edge, the central portion having a second thickness which is from 0.001 inch and which is less than the first thickness, the central portion being positioned between the interproximal surfaces of adjacent teeth when the tooth spacer is between the teeth.

13. A tooth spacer comprising:

a body having two opposite side edges extending between gingival and occlusal edges;

the body including a non-abrasive central portion of a reduced thickness; and the body including a reinforcing portion which is thicker than the central portion and which at least partially bounds the central portion, the reinforcing portion extending between the central portion and the occlusal edge and along the sides of the central portion.

14. A tooth spacer comprising:

a body having two opposite side edges extending between gingival and occlusal edges.

the body including a central portion of a reduced thickness;

the body including a reinforcing portion which is thicker than the central portion and which at least partially bounds the central portion the reinforcing portion extending between the central portion and the occlusal edge and along the sides of the central portion; and wherein the central portion has a thickness which is no greater than 0.001 inch.

15. A tooth spacer for positioning between the interproximal surfaces of a pair of adjacent teeth during a dental procedure, the teeth having a proximate area where the teeth of the pair are closest to or in contact with one another, the tooth spacer comprising:

a monolithic body with a tooth proximate surface receiving recess extending from one edge of the body toward an opposite edge of the body and being spaced from the opposite edge by a portion of the body such that said portion of the body reinforces the recess, the body having first and second leg portions on either side of the recess which reinforce the recess, the body being positioned between the pair of teeth with the recess positioned between the proximate surface between the adjacent teeth and the first and second leg portions being positioned on either side of the proximate surface, when the spacer is inserted between the adjacent teeth.

16. A tooth spacer according to claim 15 wherein the first and second leg portions each have a first side edge bounding the recess and a second side edge spaced from the recess, and wherein the second side edges are blunt.

17. A tooth spacer according to claim 15 comprised of stainless steel.

18. A tooth spacer for positioning between the interproximal surfaces of a pair of adjacent teeth during a dental procedure, the teeth having a proximate area where the teeth of the pair are closest to or are in contact with one another, the tooth spacer comprising:

a body with a tooth proximate surface receiving recess extending from one edge of the body toward an opposite edge of the body and being spaced from the opposite edge by a portion of the body such that said portion of the body reinforces the recess, the body having first and second leg portions on either side of the recess which reinforce the recess, the body being positioned between the pair of teeth with the recess positioned between the proximate surface between the adjacent teeth and the first and second leg portions being positioned on either side of the proximate surface, when the spacer is inserted between the adjacent teeth; and wherein the first and second leg portions have outer side edges which are in the form of a rounded lip.

19. A tooth spacer according to claim 18 wherein the lip comprises rubber.

20. A tooth spacer according to claim 18 wherein the lip comprises a polymer material.

21. A tooth spacer for positioning between the interproximal surfaces of a pair of adjacent teeth during a dental procedure, the teeth having a proximate area where the teeth of the pair are closest to or are in contact with one another, the tooth spacer comprising:

a body with a tooth proximate surface receiving recess extending from one edge of the body toward an opposite edge of the body and being spaced from the opposite edge by a portion of the body such that said portion of the body reinforces the recess, the body having first and second leg portions on either side of the recess which reinforce the recess, the body being positioned between the pair of teeth with the recess positioned between the proximate surface between the adjacent teeth and the first and second leg portions being positioned on either side of the proximate surface, when the spacer is inserted between the adjacent teeth; and wherein the tooth proximate area receiving recess portion of the body is from 0.0001 to 0.001 inch thick.

22. A tooth spacer according to claim 21 in which the leg portions of the body are 0.0015 to 0.003 inch thick.

* * * * *